United States Patent [19]

Wiktorowicz

[11] Patent Number: 5,593,559

[45] Date of Patent: Jan. 14, 1997

[54] ON LINE ION CONTAMINANT REMOVAL APPARATUS AND METHOD FOR CAPILLARY ELECTROPHORESIS

[75] Inventor: John Wiktorowicz, San Jose, Calif.

[73] Assignee: The Perkin-Elmer Corporation, Foster City, Calif.

[21] Appl. No.: 372,737

[22] Filed: Jan. 13, 1995

Related U.S. Application Data

[62] Division of Ser. No. 186,080, Jan. 25, 1994, Pat. No. 5,423,966.

[51] Int. Cl.$^6$ .......................... G01N 27/26; G01N 27/447
[52] U.S. Cl. .......................... 204/453; 204/455; 204/604; 204/605
[58] Field of Search .......................... 204/601, 602, 204/603, 604, 605, 451, 452, 453, 454, 455

[56] References Cited

U.S. PATENT DOCUMENTS 5,085,756  2/1992  Swedberg .......................... 204/605
5,246,577  9/1993  Fuchs et al. .......................... 204/605 X

OTHER PUBLICATIONS

Aebersold et al. Journal of Chromatography, 516: 79–88 (1990) No Month Available Analysis of dilute peptide samples by capillary zone electrphoresis.

*Primary Examiner*—Kathryn Gorgos
*Assistant Examiner*—John S. Starsiak, Jr.
*Attorney, Agent, or Firm*—Paul D. Grossman; John R. Wahl

[57] ABSTRACT

A Capillary Electrophoresis apparatus and method are disclosed which utilize a meltable plug in an end of the capillary tube to selectively pass small ionic contaminants electrophoretically and retain macromolecular analytes against one end of the plug until the plug is melted. When this plug is melted, the analytes and the contaminants pass through unimpeded. This permits separation of the analytes from the contaminants during electrophoretic separation and enhances instrument resolution.

9 Claims, 2 Drawing Sheets

ON LINE ION CONTAMINANT REMOVAL APPARATUS AND METHOD FOR CAPILLARY ELECTROPHORESIS

This application is a division of application Ser. No. 08/186,080 filed Jan. 25, 1994 now U.S. Pat. No. 5,423,966.

BACKGROUND OF THE INVENTION

1. Field of the Invention

The present invention relates generally to separation of molecular components in a fluid sample and, in particular, to an apparatus and a method for separating ion contaminants from analytes of interest in a sample fluid in an electrophoresis column.

2. Description of the Related Art

Electrophoresis is widely used for fractionation of a variety of biomolecules, including nucleic acid species, proteins, peptides, and derivatized amino acids. One electrophoretic technique which allows rapid, high resolution separation is capillary electrophoresis (CE). Typically, fused silica tubes are used in CE. These tubes are filled with a separation medium, e.g. a buffer solution or a polymer matrix such as is described in co-owned U.S. Pat. Nos. 5,164,055; 5,126,021; 5,096,554; and 5,015,350 in free-solution capillary electrophoresis or, a gel such as an agarose gel.

A CE system basically comprises an injection system, a separation system consisting of the capillary tube and buffer reservoirs in a temperature regulated compartment, a high voltage power supply, a detector, and a data processing system. The injection system generally consists of an automated mechanism that allows for both hydrodynamic (vacuum or pressure) and electrokinetic (electromigration) injection of a buffer and a sample into one end of the capillary tube. The temperature regulated environmental compartment or enclosure may contain components of the injection system as well as the capillary tube. The enclosure provides a precisely controlled environment for the capillary, ensuring that the Joule heat generated during CE is efficiently dissipated and ensuring pH stability and constant viscosity of the CE medium. The high voltage power supply typically supplies an electrophoretic driving potential of up to 30 KV between the ends of the capillary tube. The detection system is usually an ultraviolet (UV) absorbance or fluorescence based detector. The instrument data system may consist of a chart recorder or computer based data acquisition system.

To perform CE, a fluid sample volume is either hydrodynamically or electrokinetically loaded, i.e. drawn into the separation medium in one end of the capillary tube. An electric field is then applied between the ends of the tube to electrophoretically draw the charged analytes in the sample through the separation medium separating the sample components in accordance with each of the analyte's electrophoretic mobility. Molecular separation within the separation medium may be based on molecular size, in the case of nucleic acid species (which have about the same charge density), or on a combination of size, shape, and charge, in the case of proteins and peptides.

It is well known that, for many charged biopolymers of interest, e.g., single- and double-stranded DNA and sodium dodecyl sulfate (SDS)-denatured proteins, separations based on differences in electrophoretic mobilities in free solution are not possible. Therefore, in order to effect electrophoretic separations of mixtures of these molecules, one has to employ a medium which exploits the frictional characteristics of these species in such a way as to enhance the molecular size dependence of electrophoretic mobility. A free solution separation medium containing an entangled polymer may be designed for this purpose. The separation medium polymer concentration and/or degree of crosslinking between the polymer molecules in such mediums may be varied to provide separation of species over a wide range of molecular weights and charges. Low viscosity entangled polymer solutions such as are disclosed in U.S. Pat. No. 5,126,021 have also been used to separate large DNA fragments and proteins.

Another alternative is to use a solid gel separation medium. For example, one preferred temperature solidified separation media is agarose gel, typically used for separating nucleic acid fragments greater than about 1000 bases, where the concentration of the agarose may vary from about 0.3%, for separating fragments in the 5–60 kilobase size range, up to about 2%, for separating fragments in the range of 100–3000 base pairs. A cross-linked polyacrylamide gel separation medium is typically used for separation of smaller size fragments, typically less than about 1000 base pairs. However, DNA restriction fragments ranging from 72 to 1353 base pairs (bp) have been separated by CE in 0.3–2.0% solutions of agarose gel at 40° C. by Bocek et al, *Electrophoresis* 12:1059 (1991). Chen et al, *Clinical Chemistry* 37:14 (1991) describes separation of proteins using an agarose separation medium.

One difficulty with separations of macromolecules in capillary electrophoresis using either free solution or gel mediums is band broadening caused by spatial interference of migrating charged contaminant ions in the sample mixture with the analytes. These contaminants may be removed by desalting the sample prior to electrophoresis. Schwartz et al, *Journal of Chromatograhpy* 559:267 (1991) teaches desalting, i.e. the removal of small ion contaminants, from a capillary electrophoresis column by ultrafiltration of the sample prior to detection of DNA restriction fragments by CE. This ultrafiltration technique is a separate distinct step, performed prior to introduction of the sample solution into the CE column. Such a step takes a Substantial amount of time and carries with it the potential for handling errors and contamination to be introduced into the sample solution if not rigorously performed.

There is thus a need for an apparatus and method which avoids the necessity of a separate desalting step prior to loading the sample into a CE column.

SUMMARY OF THE INVENTION

It is thus an object of the invention to provide an apparatus and method to remove small ions from an electrophoresis sample mixture after the sample has been loaded in one end of an electrophoresis column such as a slab gel or capillary tube.

It is a further object of the invention to provide a method and apparatus to concentrate the analytes in an electrophoresis sample mixture at the entrance to the separation medium prior to electrophoresis of the analytes.

The preferred apparatus in accordance with the invention is a modified form of a conventional capillary electrophoresis apparatus such as is disclosed in U.S. Pat. No. 5,207,886, which includes an automatically temperature controlled environmental chamber preferably housing the samples to be analyzed, buffer containers, a vial containing a meltable plug material, the capillary tube, an automated sample handling system and the detector; a high voltage power supply; and a programmable computer for controlling the various motors and valves of the sample handling system and for controlling the temperature of the environmental chamber.

The automated sample handling system includes a means, in the case of free solution CE and in the case of an agarose gel being used as the separation medium, for introducing a melted plug, typically an agarose gel material in a liquified state, into one end of the capillary tube in advance of sample introduction into the capillary. The system more particularly transfers the end of the capillary tube between the sample container, a buffer solution container and a vial containing the plug material in accordance with signals from the computer. In the case of CE in which a rigid gel separation medium such as an acrylamide gel is used, the meltable plug is preinstalled in one end of the capillary tube.

The general method of fractionating charged analyte species in a sample containing small ions that are capable of interacting and interfering with separation of the species by electrophoresis in accordance with the invention involves the following steps:

a) interposing between an electrophoretic separation medium and an analyte-application or entrance region, a barrier layer of material having a low temperature gel state effective to block, or at least substantially retard, electrophoretic migration of the analyte species therethrough, and a high-temperature liquid state;

b) loading the sample into the analyte-application region and onto the barrier layer;

c) placing an electric potential across the barrier layer, while the layer is in the gel state, to produce electrophoretic separation of the small ions from the analyte species in the sample;

d) heating at least the barrier layer to a liquid state, with continued application of the electric potential to allow migration of the analyte species through the barrier layer and into the electrophoretic separation medium; and e) electrophoretically separating the analyte species in the medium.

This method is particularly applicable to capillary electrophoresis. More specifically, the preferred method in accordance with the present invention basically involves introducing a meltable plug, which is effective to block passage of analyte species of interest only when solidified, i.e. gelled, into one end of the CE capillary tube which has a separation medium therein, placing the plugged end of the capillary tube into a liquid sample containing the analyte species of interest and ionic contaminants, i.e., small ions that are capable of interacting with and interfering with analyte separation, drawing the sample into the capillary tube against the plug, placing the ends of the capillary tube into buffer solutions, applying an electrical potential between the ends of the tube to generate an electric potential across the plug and the separation medium to electrophoretically draw the contaminants through the plug and at least partially through the medium in the capillary tube, and raising the temperature of the plug to melt the plug and electrophoretically draw the analytes through the capillary tube to the detector.

If the separation medium is a flowable solution, an entangled polymer solution, or also a melted agarose gel, the plug may be cooled to a gelled state after hydrodynamically drawing the sample into the capillary tube. This permits a volume of the sample to be introduced into the tube adjacent the plug prior to CE. If the separation medium is a solidified gel, the medium cannot be displaced in the tube during sample introduction. Accordingly, in these cases, the plug is installed in the capillary tube in advance of CE along with the separation medium, and sample introduction must be done electrokinetically. A volume of buffer solution or separation medium is preferably placed in the tube against the upstream end of the plug to provide room adjacent the end of the plug for concentrating the analytes.

The meltable plug or barrier layer substantially retards migration, effectively blocking passage of the analytes through the capillary tube when the plug is gelled and the electrical potential is applied between the ends of the tube and thus across the plug and separation medium. The plug is transparent, however, to the contaminant ions. When the plug is melted, the plug material either electroosmotically flows through the capillary tube along with the analytes of interest, i.e. in free solution and entangled polymer CE, or the plug remains stationary against the separation medium if the medium is a rigid gel. In either case, the melted plug material is simply transparent to the analytes as well as the contaminant ions. These and other features, advantages, and objects of the invention will become more apparent from a reading of the following detailed description when taken in conjunction with the accompanying drawing.

DETAILED DESCRIPTION OF THE INVENTION

Figure 1:
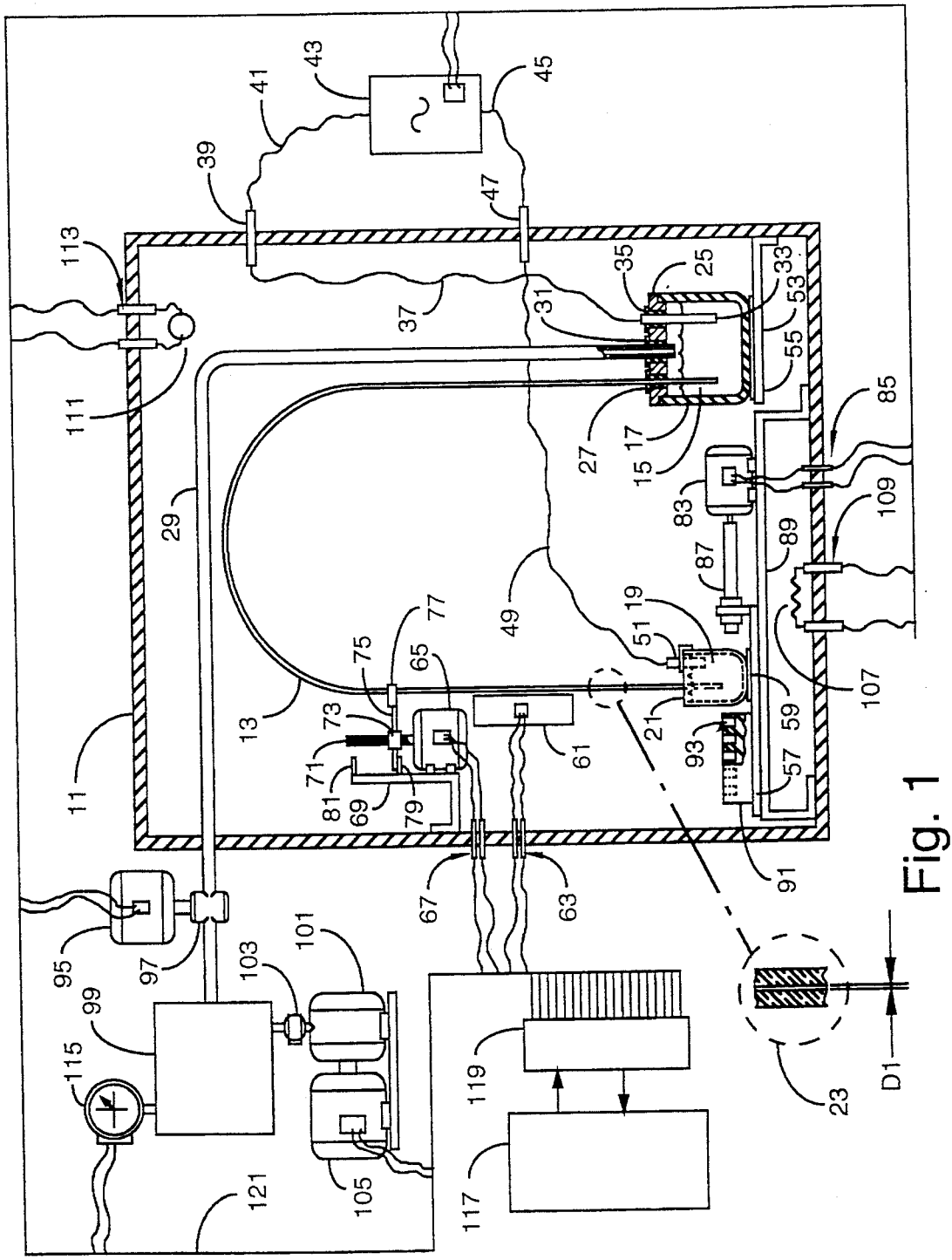
FIG. 1 is a schematic diagram of a capillary tube electrophoresis system used in practicing capillary electrophoresis in accordance with the invention.

FIG. 1 is a partially sectioned illustration of an embodiment of an automated capillary electrophoresis, henceforth CE, apparatus according to the invention. The apparatus includes an environmental enclosure 11, which has access openings (not shown), and feedthroughs of various kinds through the walls of the enclosure 11 for internal elements that must be connected to elements outside the enclosure 11.

Electrophoresis is accomplished within the enclosure 11 in a capillary tube 13, preferably constructed of fused silica, such as is typically used for high sensitivity liquid or gas chromatography. View 23 is an enlargement of the capillary tube 13 in cross section The internal diameter of the capillary, D1, varies for different kinds of samples and for other reasons. D1 generally may be between zero and 200 microns. A typical value for D1 is 50 microns. The wall thickness of tube 13 allows for efficient heat transfer and is small enough that the tube is flexible and may generally be manipulated without breaking.

One end 14 of the capillary tube 13 is immersed in a first buffer solution 19 held in a first container 21. The other end of the capillary tube 13 is immersed for the duration of the process in a second buffer solution 15 in a second container 17. Buffer solutions 15 and 19 are typically the same solution, and many are well known in the art.

Second container 17 preferably has an airtight top 25 to preclude evaporation. Capillary tube 13 enters the second container through a stopper 27 maintaining an airtight seal. There are two additional penetrations through top 25. A hollow tube 29 enters through a stopper 31 and an electrode 33 enters through another stopper 35. Stopper 35 is typically made of an electrically non-conducting material. An electrical lead 37 goes from electrode 33 to an insulated electrical feedthrough 39 which allows an electrical signal or power to cross the wall of the enclosure 11 without shorting to the enclosure. On the outside, electrical lead 41 goes to one terminal of a high voltage power supply 43. Another electrical lead 45 goes to another feedthrough 47 from an opposite terminal of the power supply 43. A lead 49 inside the enclosure 11 goes from the feedthrough 47 to an electrode 51 attached to and positioned with the end 14 of the capillary tube 13 immersed in the first buffer solution 19 in the first container 21.

The electrode 51 and the end 14 of the tube 13 move together throughout the following discussion. The ends of the tube 13 are initially immersed in the buffer solution in the two buffer containers 17 and 21. The power supply 43, through the electrical leads, feedthroughs and electrodes, is used to maintain an electrical potential between the ends of the capillary tube 13.

The second container 17 rests on a support 53 with an electrical insulator 55 between the container and the support. The insulator 55 is needed if the container and support are electrically conductive. First container 21 rests on an insulator 59 on a movable, sliding support 57 for a similar reason.

A detector 61 is positioned adjacent to one portion of the capillary tube 13 to measure the results of electrophoresis in the capillary tube. Such detection instruments are well known in the art, and include for example an Applied Biosystems Model 783 Spectroflow UV/Visible Detector, which is a variable wavelength programmable detector that is specifically adapted for on-column detection. Electrical leads through feedthroughs 63 carry power and signals for the instrument. There may be more than the two leads shown.

An automatic sample handling system is incorporated into the apparatus to handle multiple samples. Thus, when the electrophoresis process is complete on one sample, and another sample is wanted in the capillary tube 13 for analysis, a new sample may be loaded without manual intervention or disturbing the environmental enclosure 11.

A motor 65, controlled by computer 117 via leads through feedthrough 67 and supported by bracket member 69 is activated to turn lead screw 71. Nut 73 supports an arm member 75 which has a clamp 77 securely holding capillary tube 13, so that turning lead screw 71 will raise and lower the nut 73 and, in turn, tube 13. The vertical travel of nut 73 is determined by the distance between stops 79 and 81. This distance is set to be sufficient for the lower end of the capillary tube 13 along with the electrode 51 to be raised above the rim of the container 21, and lowered again. With tube 13 raised above the rim of the container 21, a pair of motors 83 (one of which is not shown) may be actuated by the computer 117, one of the motors 83 activated via leads through feedthroughs 85 to turn lead screw 87 moving support 57 horizontally along support 89 in an "x" direction. Similarly, the other motor 83 and lead screw (not shown) translates the sliding support 57 horizontally in a "y" direction transversely to the "x" direction, for x-y positioning of the support 57 under the end 14 of the capillary tube 13.

A sample container tray 91 with multiple microvolume sample containers 93, arranged in at least one row in the container tray 91, and more typically in an 8×12 array, is prepared in advance and placed adjacent to the container 21 on the sliding support 57. Each sample container 93 may contain a sample to be analyzed.

A sample may be hydrodynamically drawn into the capillary tube 13, e.g., by pressurizing container 21 or by drawing a vacuum on the opposite end of the tube. The embodiment of the apparatus of the invention shown in FIG. 1 uses the second approach, a relative vacuum is drawn in second container 17 by means of tubing 29 which exits the environmental enclosure 11 and is connected to a vacuum reservoir 99 to introduce a new sample into the capillary tube 13, while one end of the capillary 13 is in one of the microvolumes 93 of sample material. A valve motor 95 controlled by computer 117 rotates a three-way rotary valve 97 to connect the tubing 29 to the vacuum reservoir 99 to draw a vacuum in the container 17. The reservoir is maintained at desired vacuum level by vacuum pump 101 through isolation valve 103. A vacuum sensing gauge 115 with programmable signal points monitors the vacuum level in reservoir 99. The vacuum pump is powered by motor 105. Careful control of timing and vacuum level provides a very accurate method for drawing a predetermined amount of sample material into the capillary tube 13. As an example, using a pressure differential of 5.0 in. of Hg between the vacuum reservoir and the enclosure 11, with a 65 cm long fused silica capillary filled with a buffer solution and having a 50 micron inside diameter, a 2 second open time for valve 97 results in an injection quantity of 5 nanoliters of an aqueous solution. Typical injection volumes range from 1 nl to 10 nl in this preferred embodiment, although other size samples could, of course, be chosen depending on the size of the reservoir used to hold the sample and the size internal volumetric of the capillary tube 13.

The following discussion, for simplicity, assumes that the separation medium in the capillary tube is a buffer solution or entangled polymer solution. Distinctions for rigid gel separation media will be made where appropriate. When a new sample is drawn into the one end 14 of the capillary tube 13, the vacuum is removed from container 17, the capillary tube end 14 and electrode 51 are again raised, the container 21 is returned to a position in registry under the capillary tube 13, and the end 14 of the capillary tube 13 and electrode 51 are re-immersed in the buffer 19 by lowering the tube 13 via energizing motor 65.

The container tray 91 preferably also includes a vial 94 containing a meltable plug material such as an agarose gel if the electrophoresis separation medium being utilized is a buffer or entangled polymer solution. The vial 94 may alternatively be a separate container or trough located on the slide 57 adjacent the container 21 and the sample array container 91. If the separation medium is an acrylamide gel, the meltable plug must be preinstalled in the end 14 of the capillary tube 13 and therefore a vial 94 is not required.

Figure 2:
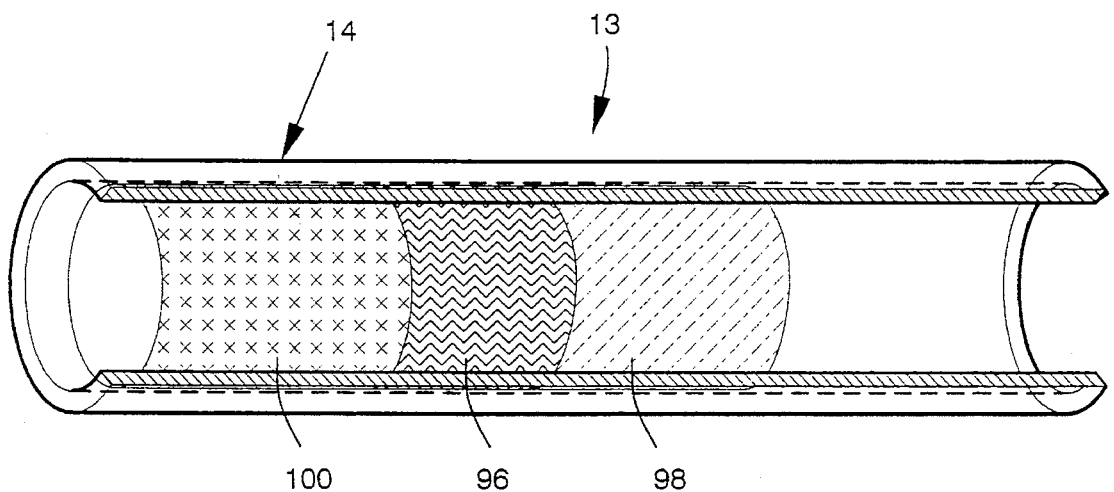
FIG. 2 is an enlarged view of the inlet end of a capillary tube showing the meltable plug in accordance with the invention.

The plugged end 14 of the capillary tube 13 is shown enlarged and in section in FIG. 2. The meltable plug 96 in the end 14 is sandwiched between the separation medium 98 and a receiving volume 100 of separation media or buffer solution. If a flowable liquid such as a buffer solution or entangled polymer solution is the separation medium, then the receiving volume 100 will also be a flowable liquid and the plug 96 will be sandwiched by the separation medium. If, however, the separation medium 98 is a gel which cannot readily move through the capillary tube, then the volume 100 may be filled with a buffer solution or, alternatively, the plug may be positioned flush with the end of the tube. A volume 100 of buffer solution is preferable to permit concentration of the analyte against the upstream face of the meltable plug 96 during electrokinetic sample loading.

An important aspect of the preferred apparatus according to the invention is that the temperature inside the environmental enclosure 11 is automatically and accurately controlled and cycled by computer 117 to melt or solidify the plug of meltable material in the end 14 of the capillary tube 13 at a predetermined, user-defined time in order to separate the analytes of interest from the contaminant ions in the sample. A heating element 107 is powered through feedthroughs 109 to provide heat, and a heat sensing element 111 monitors temperature through leads 113. Cooling is provided by chiller 108 connected to cooling coils 110 in the environmental chamber 11. A fan 112 may also be provided in the chamber 11 to circulate the internal air to achieve a uniform temperature throughout the chamber 11. The amount of heating and cooling required is determined by the computer 117 into which is fed the desired temperature protocol for use during CE by the user and the actual enclosure temperature via temperature sensing element 111.

The apparatus in accordance with the present invention shown in FIG. 1 operates as follows for free solution CE. First, the sample containers 93 and the meltable plug vial 94 are prepared in the tray 91 and placed inside the environmental chamber 11 on the platform 57. The environmental chamber 11 is then closed.

The computer 117 then automatically initiates and controls the following actions. The capillary tube 13 is lowered into the buffer container 21 and a vacuum is established in the container 17 by the computer sending a signal to open valve 97 in order to draw the buffer solution through the capillary tube 13 if the tube has not previously been filled. The vacuum is then removed from the container 17. The motor 65 is then energized to raise the end of the tube 13 out of the container 21. When the stop 81 is reached, the motor 65 is de-energized and the motor 83 is energized to translate the platform 57 in the "x" direction to a position at which the tube 13 is in registry over the vial 94.

The motor 65 is again energized in the opposite direction to lower the end 14 of the tube 13 into the vial 94. When the lower stop 79 is reached, motor 65 de-energizes and the temperature of the chamber 11 raised, if not done previously, to at least the melting temperature of the plug material in the vial 94, for example, 45 degrees C, to melt the plug material. When this temperature is reached, a vacuum is then drawn in container 17. This vacuum causes a volume 96 of melted plug material to be drawn from the vial 94 into the end 14 of the capillary tube 13. The vacuum is then removed and the capillary tube 13 is raised out of the vial 94. Any one of the microvolume sample containers 93 or the vials 94 of the container tray 91 may be selectively moved via computer control to a position directly beneath the raised end 14 of the capillary tube 13 and the electrode 51. The end 14 and the electrode 51 may then be lowered into either the sample container 93 or vial 94 by computer control of motor 65.

There are two options for sample loading for free solution EC. First, the sample may be loaded electrokinetically. This method concentrates the analytes against the end face of the plug 96. Second, the sample may be loaded hydrodynamically as above described. Alternatively, to achieve the same result, a seal may be provided on container 21 and container 21 pressurized to push a sample into the end 14 of the capillary tube 13. If the separation medium is a rigid gel, however, the sample must be electrokinetically loaded. Electrokinetic loading is preferred in either case.

The volume 100 of buffer should be provided in the end 14 of the capillary tube 13 adjacent the plug 96 if the sample is to be loaded electrokinetically to permit concentration of the analytes. Accordingly, the platform 57 is again translated via motor 83 to position the capillary tube 13 over the buffer container 21. The tube 13 is lowered into the buffer solution 19 and a vacuum is established again in container 17 to hydrodynamically draw a predetermined volume of buffer into the end of the tube 13. The vacuum is then removed from the container 17, the capillary tube 13 raised out of the container 21, and the platform 57 again translated to a position in registry above one of the sample containers 93.

The temperature in the chamber 11 is then lowered to a temperature below the solidification or gelling temperature of the plug 96 material. The end 14 of the capillary tube 13 is then lowered into the sample container 93. A sample is drawn into the buffer volume 100 just established in the end 14 of the capillary tube 13 electrokinetically by establishing an electrical potential between the sample container 93 and the buffer container 17 at the other end of the capillary tube 13 via the high voltage power supply 43 through lead 121, pass through 123, and lead 125 connected to the electrode 51 alongside end 14. During electrokinetic loading, the analytes concentrate on the end surface of the solidified plug 96 in the capillary tube 13 and the charged contaminant ions pass right through the plug into the separation medium 98.

If, on the other hand, the sample is to be hydrodynamically loaded, the volume 100 is eliminated and the plug 96 is located flush with the end 14 of the tube 13. The plug must remain liquid at this point. The end 14 of the capillary tube 13 is lowered via motor 65 into the sample container 93 prior to lowering the chamber temperature below the solidification temperature of the plug. A vacuum is applied to the buffer container 17, drawing the sample from the sample container 93 into the tube 13 and moving the still liquid plug 96 and the separation medium further into the tube 13. Alternatively, a positive pressure could be applied to container 21 to push the sample, liquid plug, and separation medium further into the tube 13. This process does not concentrate the analytes.

The vacuum is then removed as above described and the end 14 of the capillary tube 13 raised out of the sample container 93 and lowered again into the buffer container 21. The temperature of the enclosure 11 is then lowered to solidify the plug 96. A high voltage is then applied to electrodes 51 and 33 to draw the ion contaminants through the plug 96 into the separation medium 98. At a predetermined subsequent time, the temperature of the enclosure 11 or specifically the plug 96 is raised to melt the plug 96, allowing electrophoretic passage of the analytes to proceed through the melted plug 96 and through the separation medium 98 and past the detector 61.

The operative steps of the preferred method of the invention may be summarized as basically the steps of 1) providing melted plug 96 which is effective to substantially retard passage of analytes of interest only when solidified, i.e. gelled, in one end 14 of the CE capillary tube 13 filled with a separation medium 98, 2) cooling the capillary tube 13 to gel the plug 96, 3) placing the end 14 of the capillary tube 13 into a liquid sample 93 containing the analytes of interest and ionic contaminants, applying an electrical potential between the ends of the tube to electrophoretically draw the contaminants through the plug and at least partially through the capillary tube 13, and 5) raising the temperature of the chamber to melt the plug, and 6) electrophoretically drawing the analytes through the capillary tube 13 to the detector 61.

Step 1 of the method just described more preferably includes the step of introducing a volume 100 of a buffer solution 19 immediately after introduction of the melted plug into the capillary tube 13 and prior to cooling the capillary tube 13 to gel the plug 96. This buffer volume in turn provides a space in the end 14 of the capillary tube 13 adjacent the plug 96 to receive and concentrate the analytes in the sample against the surface of the gel plug 96 during electrokinetic loading of the sample.

The method more preferably includes the steps of 1) introducing a melted plug material which is effective to block passages of analytes of interest only when solidified into a tube filled with a separation medium; 2) cooling at least the plug material to gel the plug 96; 3) placing the end 14 of the capillary tube 13 into a liquid sample 93 containing the analytes of interest and at least one contaminant; 4) drawing a portion of the sample 93 into the capillary tube; 5) placing the ends of the capillary tube into the buffer solutions 15 and 19; 6) applying an electrical potential between the ends of the capillary tube to electrophoretically draw the contaminants through the plug and at least partially through the capillary tube 13, raising the temperature of the plug to melt the plug; and 7) electrophoretically drawing the analytes in the sample through the melted plug and through at least a portion of the capillary tube 13.

When the high voltage is applied between the ends of the capillary tube, the contaminants begin to pass through the plug 96 and into the separation medium 98. After the contaminants have traveled through the capillary tube sufficiently to preclude interference with the analytes during detection, the capillary temperature may be raised to melt the plug 96. When the plug melts, the plug material and the analytes electrophoretically pass through the capillary tube if the medium is a free solution, i.e. a buffer or entangled polymer solution. Otherwise, only the analytes and contaminants pass through the tube.

As previously stated, the separation medium 98 in the tube may be a buffer solution or an entangled polymer solution used in free-solution capillary electrophoresis, or a rigid gel. The meltable plug 96 may be any material which melts at a specific temperature and which has the ability to selectively retard migration of analytes during the injection and subsequent steps. The meltable material may be any polymer colloid which has a lower temperature gel phase and a higher temperature liquid phase. The meltable plug 96 is preferably an agarose gel material which becomes liquid at a specific temperature, for example, about 45° C. The liquid plug is injected at or above that temperature hydrodynamically into the capillary tube which has been previously loaded with a separation medium which may also be an agarose gel having a higher melting temperature, for example, about 50° C. In this latter case, hydrodynamic plug injection would have to be done at a temperature above the melting temperature of the separation medium. In either case, injection of the liquid agarose gel plug is preferably immediately followed by introduction of a volume 100 of buffer solution. This provides a volume inside the entrance end of the capillary tube for analyte concentration The temperature of the capillary tube is then lowered below the solidification temperature of the agarose gel plug 96 (and the separation medium if it is a rigid gel) so that the crosslinking of the gel plug is of sufficient magnitude that macromolecules are not permitted to migrate freely through the plug; however, small molecules may migrate unimpeded through the plug and the separation medium. The plugged end 14 of the capillary tube 13 is then inserted into a sample container 93 containing analytes of interest. The sample is then loaded electrokinetically into the capillary tube. By applying a voltage between the ends of the tube, the charged molecules migrate into the capillary. The macromolecules stack against the surface of the gel and the small ions continue migration through the separation medium in the capillary tube. At some subsequent point in time the temperature of the solidified gel plug is raised to the melting temperature of the agarose gel plug and electrophoresis of the concentrated macromolecules begins, now free of small molecule contamination.

It is not necessary to completely flush all the small contaminant molecules through the separation medium before raising the plug temperature. Only a sufficient amount of time is required so that the most mobile macromolecule does not electrophoretically overtake the small contaminant molecules prior to reaching the detection region of the capillary tube.

The entire capillary tube 13 may be heated and cooled to achieve the separation of the small molecules as described above. Alternatively, only the capillary portion containing the gel plug 96 may be heated and cooled separately from the portion of the capillary tube containing the separation medium 98. However, for stability and viscosity considerations, it is preferred that the overall temperature of the capillary, e.g. the enclosure 11 be heated and cooled. Viscosity and therefore electrophoretic mobility are often strong functions of temperature, so that for desired reproducibility in the system, temperature uniformity is preferred.

Power and control leads for all the electrical equipment associated with the apparatus of the preferred embodiment are carried by electrical conduit 121 to a control interface 119 which provides power terminations and switching of signals for control purposes. The control interface 119 is connected to and manipulated by the computer 117 which can be pre-programmed so that critical parameters may be maintained and sequences of analyses may be performed automatically by the apparatus.

For example, the vacuum level desired can be entered by the operator as control data, and the computer 117, through the control interface 119, monitors the signal from vacuum gauge 115 and opens and closes vacuum isolation valve 103 so that the desired vacuum level is closely maintained. Similarly, the computer 117 is used to control the temperature inside the environmental enclosure by monitoring temperature sensor 111 and controlling power to heating element 107 or the cooling device 108 as needed to maintain the programmed temperature. Also, the computer can be programmed to allow a sequence of analyses to be made, using the several samples preloaded into the sample containers 93 in the container tray 91, controlling the electrical devices in the required sequence. The computer program may be set to run analyses on all of the microvolume samples, one-after-the-other, or to allow for manual intervention and initiation between each analysis.

It will also be appreciated by those skilled in the art that there are several ways to control the temperature of the solvent/solute system and the plug 96. For example, one way has already been described which uses a heater and cooling system to control the interior of the environmental chamber 11. Another approach would be to use one or more electrical heaters wrapped around the capillary tube. Those skilled in the art will undoubtedly be able to think of other equivalent methods for controlling the temperature to effect electrophoretic mobility. Those skilled in the art will also understand that in some instances it may be preferred to not have all components inside the enclosure 11. For example, the detector sometimes may be located outside the enclosure along with the corresponding portion of the capillary where the UV detection is to take place. Such an approach would facilitate service of the UV detector system. Also, instead of raising and lowering the capillary, one could raise and lower the sliding support to insert and remove the capillary from the sample and buffer reservoir. It should also be apparent that one could use electrophoretic media other than aqueous solutions, for example organic fluids could also be used, a specific example being acetonitrile.

One alternative application of the present invention involves the electrophoretic analysis of serum. In this case, the small molecules are the analytes of interest and the large proteins, etc., are the contaminants. When the macromolecules are restrained by the plug, the smaller molecules, the analytes of interest, can be electrophoresed past the detector. The plug may then be melted and the large molecules, proteins, etc., flushed through the capillary tube in the case of a free solution or entangled polymer medium or electrophoresed through a rigid gel medium and the tube prepared for loading a subsequent sample.

While the invention has been described with reference to particular embodiments thereof, it should be apparent that the apparatus and method may be practiced other than as specifically described. For example, although a capillary electrophoresis apparatus has been shown and specifically described, the method of the invention may be applied to other physical arrangements for electrophoretic separations such as a slab type gel electrophoresis apparatus, thus the embodiments of the invention are subject to modification, variation, and change without departing from the proper scope and fair meaning of the appended claims. Accordingly, it is intended to embrace all such changes, modifications, and variations that fall within the spirit and broad scope of the appended claims. All patents, patent applications, and publications cited herein are hereby incorporated by reference in their entirety.

What is claimed is:

1. An electrophoresis apparatus comprising an elongated chamber containing a separation medium in which to electrophorese a sample;

a high voltage power supply means for providing an electrical potential difference between opposite ends of said chamber;

meltable plug means positioned in one end of said chamber adjacent said medium for substantially retarding passage of analytes in said sample through said plug means into said medium only when said plug means is solid;

injection means for injecting said sample into said one end of said chamber; and heating means for selectively heating a portion of said chamber to melt said plug means.

2. The apparatus according to claim 1 wherein said chamber is a capillary tube.

3. The apparatus according to claim 2 wherein said meltable plug means is an agarose gel.

4. The apparatus according to claim 2 wherein said heating means further comprises a cooling means to cool the capillary tube and the meltable plug means.

5. The apparatus according to claim 4 further comprising a temperature controller for automatically controlling the heating means and the cooling means to vary the temperature of said capillary tube in accordance with a predetermined temperature/time profile.

6. A capillary tube for use in capillary electrophoresis comprising an elongated solid tube having an inlet end and an outlet end;

a separation medium disposed within said tube; and a meltable plug means positioned adjacent one end of said separation medium for substantially retarding passage of analytes in a sample through said plug means into said separation medium only when said plug means is solid, the meltable plug means being meltable at a temperature of about 45° C.

7. The tube according to claim 6 wherein said meltable plug is an agarose gel.

8. The tube according to claim 7 wherein said separation medium is a gel.

9. The tube according to claim 7 wherein said separation medium is a flowable solution.

* * * * *